United States Patent [19]
Asikainen

[11] Patent Number: 5,454,023
[45] Date of Patent: Sep. 26, 1995

[54] SOFT-TISSUE FILTER APPARATUS FOR A CEPHALOSTAT

[75] Inventor: Auvo Asikainen, Vantaa, Finland

[73] Assignee: Planmeca Oy, Helsinki, Finland

[21] Appl. No.: 235,686

[22] Filed: Apr. 29, 1994

[30] Foreign Application Priority Data

Jun. 15, 1993 [FI] Finland .................... 932741

[51] Int. Cl.⁶ ............................................ A61B 6/08
[52] U.S. Cl. ........................... 378/156; 378/159; 378/205
[58] Field of Search ............................. 378/156, 158, 378/159, 204, 205, 206

[56] References Cited

U.S. PATENT DOCUMENTS

| | | |
|---|---|---|
| 2,506,342 | 5/1950 | Burke . |
| 3,717,768 | 2/1973 | Edholm et al. .................... 378/156 |
| 3,755,672 | 8/1973 | Edholm . |
| 3,921,001 | 11/1975 | Edholm et al. .................... 378/206 |
| 4,167,675 | 9/1979 | Studberg . |
| 4,181,858 | 1/1980 | Moore . |
| 4,347,440 | 8/1982 | Haas . |
| 4,400,826 | 8/1983 | Preti et al. .................... 378/206 X |
| 4,442,533 | 4/1984 | Lescrenier .................... 378/206 X |
| 4,641,336 | 2/1987 | Gastrin . |
| 4,670,896 | 6/1987 | Klausz . |
| 4,882,741 | 11/1989 | Brown .................... 378/206 X |
| 5,136,627 | 8/1992 | Conrads . |
| 5,165,410 | 11/1992 | Warne et al. .................... 378/206 X |
| 5,278,887 | 1/1994 | Chiu et al. .................... 378/156 |

FOREIGN PATENT DOCUMENTS

| | | |
|---|---|---|
| 7142828 | 7/1972 | France . |
| 7730848 | 5/1978 | France . |
| 3347557 | 7/1984 | Germany . |
| 249368 | 9/1987 | Germany . |

*Primary Examiner*—David P. Porta
*Attorney, Agent, or Firm*—Jones & Askew

[57] ABSTRACT

The invention is related to a soft-tissue filter apparatus for a cephalostat, said apparatus being capable of positioning the patent (P) stationary for exposing radiographic images of the skull. The apparatus comprises an x-ray source (13) whose collimated (14) x-ray beam (XR) can be directed through the skull of the patient (P) onto an x-ray film (RF) contained in a cassette (23). The apparatus further comprises a soft-tissue filter assembly (10) in which to the region of one side (a) of the x-ray beam (XR) is placed an radiation-absorbing filter element (19) movable by means of a drive motor (15) transversely (B) to the x-ray beam (XR). The apparatus incorporates a light indicator unit (20) comprising a light source (25) capable of projecting onto the side of the face of the patient (P) a light marker line (LL) which is transferrable along the adjustment direction (B) of the soft-tissue filtering assembly. The light indicator unit (20) is equipped with a sensor (31) of the light marker line (LL) position, said sensor's positional information ($U_p$) being adapted in the apparatus to control the position of the soft-tissue filter element (19) to the position relative to the patient (P) indicated by means of the light marker line (LL) projected by the light indicator unit (20).

10 Claims, 3 Drawing Sheets

SOFT-TISSUE FILTER APPARATUS FOR A CEPHALOSTAT

FIELD OF THE INVENTION

The invention relates to a soft-tissue filter apparatus for a cephalostat, said apparatus being capable of positioning the patent in a stationary position for exposing radiographic images of the skull or equivalent structures. The apparatus comprises an x-ray generator whose collimated x-ray beam can be directed through the patient's skull onto an x-ray film contained in a cassette, and the apparatus further comprises a soft-tissue filter assembly in which to the region of one side of the x-ray beam is placed a radiation-absorbing filter element movable by means of a drive motor transversely to the x-ray beam.

BACKGROUND OF THE INVENTION

Conventionally known in the transmissive radiographic imaging of the skull is the use of a cephalostat available as an accessory for a panoramic x-ray apparatus. A radiographic image exposed with the help of the cephalostat is chiefly capable of presenting the bone structure of the skull alone as the soft tissues adjacent to the skull become overexposed, thus forming black areas in the image. However, a frequent need exists for taking such radiographic images of the skull in which also the soft tissues are well discernible. To this end, prior art has conventionally employed typically wedge-shaped soft-tissue enhancing filters, which are placed between the object being imaged and the x-ray film. These soft-tissue filters are operative with positioning arrangements that permit their use for locally attenuating the x-ray beam transmitted through, e.g., the patient's face, thus making the soft tissues discernible in the radiographic image. A problem herein is how to position the soft-tissue filters correctly so as to achieve the highest possible resolution in the radiographic image simultaneously for both the bone structure of the skull and the desired soft tissues adjoining thereto. Frequently, such radiographic images are so inferior in this respect that a number of re-exposures must be taken, which increases operating costs and subjects the patient to unnecessary doses of radiation.

For an attempt to solve the above-described problem, reference is made to FI patent 68515 (corresponding U.S. Pat. No. 4,641,336) filed by Instrumentarium Oy, Finland, in which a soft-tissue filter arrangement is described for use in the radiographic imaging of a patient's skull with the help of a cephalostat in which the patient is adjusted to an accurately determined imaging position by means of ear plugs or similar elements which comprise ear, nose and/or forehead supports permanently fixed with respect to the imaging coordinate system. This prior-art apparatus has means for adjusting the distance of the nose and/or forehead relative to the ear plug supports. The apparatus is disclosed to comprise output means of control information or a signal related to said distance to the end of adjusting the position of the filtering elements.

The above-described adjustment arrangement of filtering elements based on the mutual distance of the ear plug support from the forehead support or equivalent member is extremely confusing and clumsy to the user. Moreover, the use of fixed support/positioning means whose position is referenced to a predetermined coordinate system complicate the positioning of the patient by, e.g., tilting to an optimal position for maximal diagnostic value obtainable from skull exposures. Due to this drawback, radiographic exposures taken by means of the apparatus according to the FI patent are not always satisfactory, which results in a need for re-exposures, thus subjecting the patient to unnecessary doses of radiation and/or causing loss of the diagnostic value of the exposures. Further, the apparatus according to the abovementioned FI patent does not offer the implementation of individually variable soft-tissue filtering profiles.

Further references of the prior art related to the present invention can be found in U.S. Pat. Nos. 2,506,342, 3,755,672, 4,181,858 and 4,347,440 as well as in EP patent application 0,054,798 A1.

It is an object of the present invention to provide a novel type of soft-tissue filter apparatus capable of overcoming the above-discussed drawbacks and achieving the goals to be defined later in the text.

It is a further object of the invention to provide an apparatus with extremely simple operation, clear use, and fast learning, thus offering a high hit rate of exposures and elimination of need for re-exposures.

It is a still further object of the invention to provide an apparatus in which the patient can be positioned within the x-ray beam in a diagnostically optimal position without being restricted in any way by any fixed support means.

A nonlimiting further object of the invention is to provide an apparatus which is suited to implementing different kinds of variable soft-tissue filtering profiles when necessary.

To attain the above-expressed goals and those to be clarified later in the text, the invention is principally characterized by the apparatus incorporating a light indicator unit comprising a light source capable of projecting onto the side of the face of the patient a light marker line which is transferrable along the adjustment direction of the soft-tissue filter assembly and by said light indicator unit being equipped with a sensor of the light marker line position, said sensor's positional information being adapted in the apparatus to control the position of the soft-tissue filter element to the position relative to the patient indicated by means of the light marker line projected by the light indicator unit.

The use of the apparatus according to the invention is most straightforward and obvious as well as easy to learn, since the effective area of the soft-tissue filtering on the patient's skull region is accurately indicated by the light marker line.

In the apparatus according to the invention, the patient need not be positioned relative to a fixed coordinate system, but instead, the patient can be supported in a desired manner, also tilted when necessary for diagnostic reasons.

The invention is further capable of implementing different kinds of soft-tissue filtering profiles. When necessary, such profiles are controllable and variable in the vertical and/or horizontal direction by virtue of different kinds of sequential and/or superimposed light marker line/filter wedge element combinations.

The invention is next examined in greater detail by making reference to the figures of the attached drawing, which show an exemplifying embodiment of the present invention, whereby the illustrated details must not be construed to limit the applications of the invention, in which drawing:

DETAILED DESCRIPTION OF PREFERRED EMBODIMENT

Figure 1:
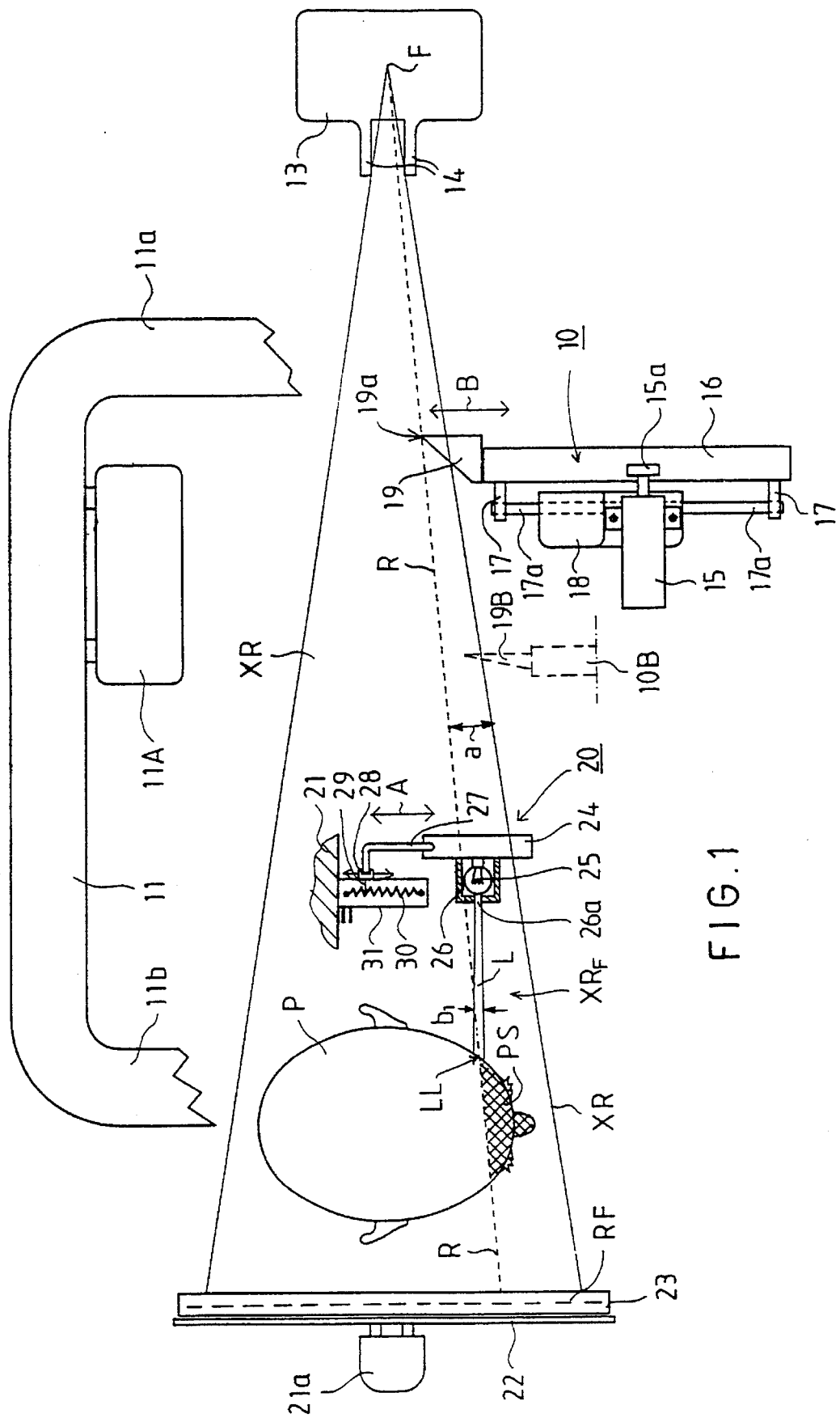
FIG. 1 is a diagrammatic top view of a cephalostat equipped with a soft-tissue filter apparatus according to the invention.
Figure 2:
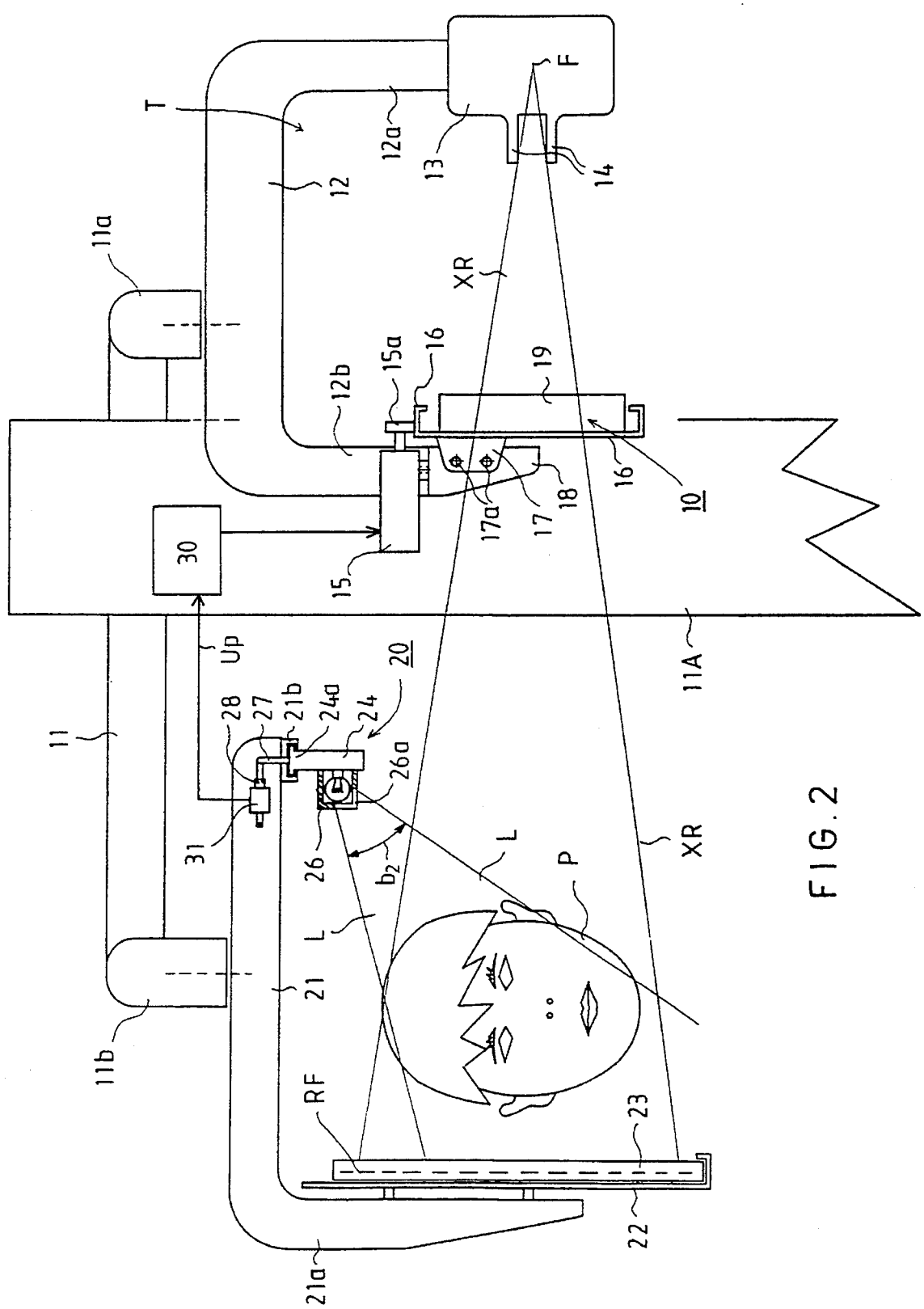
FIG. 2 is a front view of the arrangement shown in FIG. 1.

With reference to FIGS. 1 and 2, the cephalostat is shown fitted as an accessory of a panoramic tomographic apparatus suited for use in dental radiography. Using the cephalostat, transmissive radiographic skull images of a patient P are exposed. When exposing panoramic tomographic images of the patient's dental arch, the patient is positioned into a space T encompassed by a C-arm 12. The x-ray apparatus proper comprises attached to the vertical section 12a of the C-arm 12 an x-ray generator 13 equipped with a blind 14. The x-ray apparatus proper further comprises a vertical column 11A supporting a horizontal arm 11 having at its one end section 11a attached said C-arm 12, while the other end section 11b supports the body part 21 of the cephalostat. During panoramic tomographic x-ray exposures, the other section 12b of the C-arm carries a film cassette movable by means of a drive motor 15.

The cephalostat proper comprises, attached to the end section 11b of the horizontal arm 11 an arm 21 in which to the vertical section 21a at the distal end of the arm is adapted a holder 22 suited to accommodate a film cassette 23 for radiographic skull images. At the other end section 21b of the horizontal arm 21 supported by a horizontal guide 24a is mounted the body part 24 of a light indicator unit 20. The body part 24 of the light indicator unit 20 houses an electric lamp 25 surrounded by a shield/reflector 26 whose opening 26a defines the shape of the light marker beam L projected from the lamp 25. The body part 24 is adapted for manual movement along the horizontal guide 24a in the direction of arrow A by means of a handle. The light indicator unit 20 incorporates an indicator light position sensor 31 capable of reading the position of the light marker beam L. As shown in FIGS. 1 and 2, this sensor 31 is operated by connecting the slider 29 of a linear potentiometer 30 via an adapter 28 to one end of the handle 27. The body part of the sensor 31 is immovably mounted to the horizontal section of the arm 21, whereby at the movement of the light indicator unit 20 with its lamp 25 by means of the handle 27 the slider 29 of the potentiometer 30 provides a voltage Up which is linearly proportional to the position of the light marker beam L of the light indicator unit 20 in the direction of arrow A. When lit, the lamp 24 projects a line-shaped light marker beam L with a narrow sector $b_1$ in the horizontal direction and a sector $b_2$ extending vertically over the entire head height of patient P. Alternatively, the light indicator unit 20 can be implemented by designing it rotatable about its vertical axis thus achieving the adjustment of the light marker line LL.

The soft-filter assembly 10 comprises a holder member 16 which is connected by means of vertical flanges 17 to a pair of horizontal guides 17a. A wheel driven by a motor 15 transfers the member 16 in the horizontal direction indicated by arrow B, while the horizontal guides 17a move supported by sliding bushings of a body block 18 mounted to the lower end of the vertical section 12b of the C-arm 12. To the inside of the holder member 16 is attached a soft-tissue filter element 19, which in its horizontal cross section is a wedge-shaped block of absorptive material having its tip 19a extending to the region of the x-ray beam XR. The filter element 19 is made from, e.g., copper and its purpose is to attenuate the intensity of the x-ray beam XR on one side XRF of the beam in sector a. Owing to the wedge-shaped form of the filter element 19, its attenuation effect increases linearly from plane R of the wedge tip 19a toward the side of the of x-ray beam XR.

With reference to FIGS. 1 and 2, the holder member 16 shown therein acts in panoramic tomography of the dental arch as a support member for the film cassette during the exposure so that the film cassette used in panoramic exposures, as well as the filter element 19 used in skull imaging, are advantageously transferrable by the same drive motor 15 steered by the same control system, thus achieving a simple construction and cost-effective implementation of the apparatus.

Figure 3:
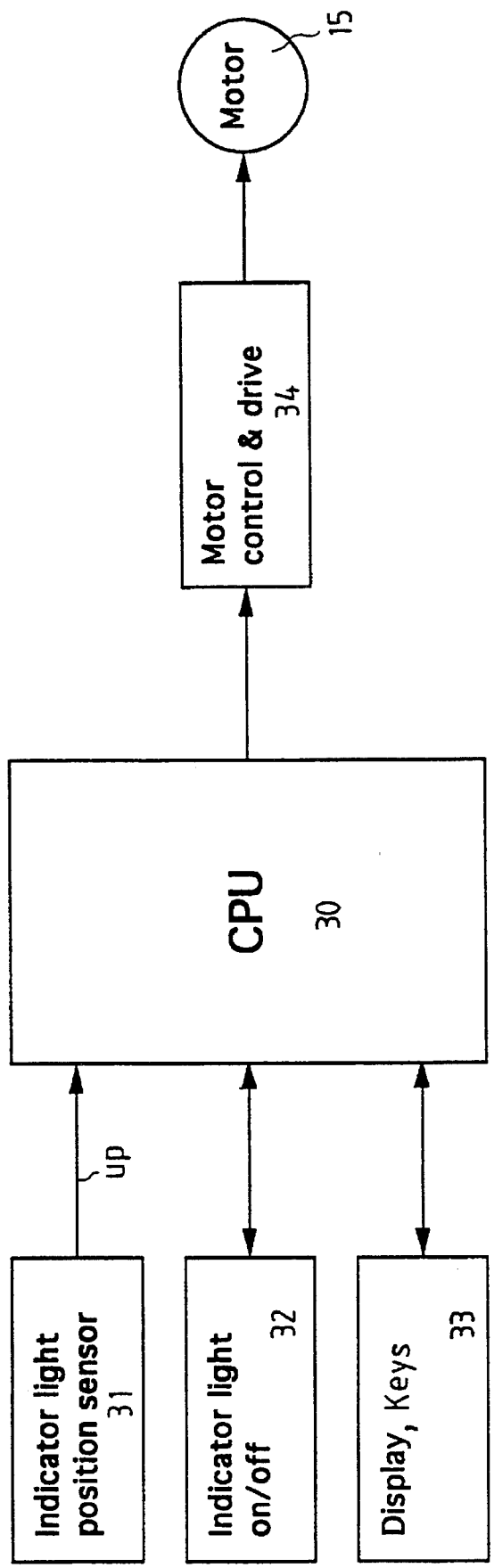
FIG. 3 is a block diagram of an apparatus according to the invention.

The function of the above-described soft-tissue filter apparatus arranged in accordance with the invention is as follows. To expose a skull image of patient P's head on an x-ray film RF, patient P is positioned and supported freely within the field of the x-ray beam XR, close to the film RF, using when necessary conventional support elements such as forehead, nose and/or ear supports or similar positioning elements suited to supporting the patient P in a position not fixed beforehand to a predetermined coordinate system. After the patient P is properly supported in a preferred position of the imaging method, tilted if necessary, current to the lamp 25 is switched on by means of the control unit 32 (FIG. 3). By shifting the lamp 25 and thus the light beam L emitted therefrom in the direction of arrow A, the light beam L is aligned on the side of the patient P's face at the point where the soft-tissue filtering is desired to start. The light beam L is seen on the patient's face as a light marker line LL which visibly and unambiguously indicates the point wherefrom the soft-tissue filtering sets on, so that the x-ray beam XR becomes attenuated by the soft-tissue filter element 19 over the area PS on the face of the patient P as indicated by the cross-hatched area in FIG. 1.

The position sensor 31 of the light indicator unit 20 issues a signal $U_p$ to a central unit 30. Subsequently, the central unit 30 controls the motor 15 via a control/driver unit 34 to transfer the tip 19a of the filter element 19 to the plane R indicated on the patient's face by the light marker line LL emitted by the light indicator unit 20. With reference to FIG. 3, the central unit 30 which is implemented with the help of a microprocessor, for instance, also communicates with a display and a keyboard 33. The display presents the exposure data and the keyboard is used for entering the necessary exposure parameters and control commands into the system.

After the above-described preparations are completed, the light beam L can be turned off and the exposure can be made on an x-ray film RF, whereby the x-ray beam XR is attenuated over the area PS on the face of the patient P, thus enhancing the reproduction of soft-tissue structures in the radiographic image on the film RF.

While a manual implementation for the movement of the light indicator unit 20 is shown in FIG. 1, the invention can also be realized by arranging the transfer and stopping movements of the light indicator unit to take place driven by the drive motor controlled via the keyboard 33.

Utilizing the principle of the invention, alternative embodiments can further be implemented in which, e.g., at least two superimposed soft-tissue filter elements $19_1$–$19_N$ (N elements) are used, each arranged to be separately movable by an individual drive motor $15_1$–$15_N$. Correspondingly, the light indicator unit 20 is adapted to house at least two superimposed light marker line units (N units), each connected to control the drive motor $15_1$–$15_N$ of its own soft-tissue filter element $19_1$–$19_N$. In this manner varied staircase and/or other stepped profiles of soft-tissue filtering can be implemented different from the straight line LL shown in the diagrams.

When necessary, also two or a greater number of filter elements acting successively (in series) can be used in a filter arrangement illustrated by an additional filter assembly 10B with its filter element 19B in FIG. 1. The filter assembly 10B can be complemented with an individual light indicator unit, whereby two or a greater number of light marker lines with, e.g., different colors can be provided, thus making it possible without the need for changing the filter element 19 to implement filter profiles in direction A different from the linear and adjustable profiles described above.

The claims of the patent application are presented in the following, whereby the different details of the invention may be varied and deviated within the scope of the claims which define the invention from those of the exemplifying embodiments.

I claim:

1. A soft-tissue filter apparatus for a cephalostat, said apparatus being capable of positioning a patient (P) stationary for exposing radiographic images of the skull or equivalent structures, to which end said apparatus comprises an x-ray source (13) whose collimated (14) x-ray beam (XR) can be directed through the skull of the patient (P) onto an x-ray film (RF) contained in a cassette (23), and said apparatus further comprises a soft-tissue filter assembly (10) in which to the region of one side (a) of the x-ray beam (XR) is placed a radiation-absorbing filter element (19) movable by means of a drive motor (15) transversely (B) to the x-ray beam (XR), characterized in that the apparatus incorporates a light indicator unit (20) comprising a light source (25) capable of projecting onto the side of the face of the patient (P) a light marker line (LL) which is transferrable along an adjustment direction (B) of the soft-tissue filtering assembly, and in that said light indicator unit (20) is equipped with a sensor (31) of the light marker line (LL) position, said sensor's positional information ($U_p$) being adapted in the apparatus to control the position of the soft-tissue filter element (19) to the position relative to the patient (P) indicated by means of the light marker line (LL) projected by the light indicator unit (20).

2. An apparatus as defined in claim 1, characterized in that the tip edge (19a) of the filter element (19) of the soft-tissue filtering assembly is wedge-shaped and is adjustable relative to a plane (R) passing through the focus (F) of the x-ray source (13) and the light marker line (LL) projected from said light indicator unit (20) onto the side of the patient's face.

3. An apparatus as defined in claim 1, characterized in that said light source (25) is adapted to project a line-shaped light marker beam (L) with a narrow sector ($b_1$) in the horizontal direction and such a wide sector ($b_2$) of the light marker beam (L) that makes the light marker beam (L) extend vertically substantially over the entire head height of patient (P) or at least over a substantial portion thereof.

4. An apparatus as defined in claim 1, characterized in that said apparatus is adapted in conjunction with a panoramic radiographic apparatus so that the same drive motor (15) is employed for transferring the soft-tissue filter assembly (10) as is used for transferring the movable fill cassette employed in the panoramic tomography of the dental arch; and that said apparatus further comprises, operative in connection with a vertical column (1 IA) of the radiographic apparatus, a horizontal arm (11) supporting a body part (21) whose one end section (21a) carries a holder (22) of the film cassette (23) used in cephalometric imaging, while the other end section (21b) of the body part supports said light indicator unit (20).

5. An apparatus as defined in claim 1, characterized in that said light indicator unit (20) comprises a body part (24) movable by manual or motorized means to move along horizontal guides (24a) in a horizontal direction (A) transversely relative to the x-ray beam (XR).

6. An apparatus as defined in claim 1, characterized in that said light indicator unit (20) is operative above the x-ray beam (XR) so as to project obliquely downwardly a light marker line (LL) which in the horizontal direction substantially has the width of a narrow line ($b_1$), while its sector in the vertical direction is multiple times wider.

7. An apparatus as defined in claim 1, characterized in that said apparatus comprises a central control unit (30), advantageously a CPU based on a microprocessor, to which unit a position sensor (31) of the light indicator unit (20) is connected, that said central control unit (30) is adapted to steer via a control/driver unit (34) the drive motor (15) of the filter element (19) of the soft tissue filter assembly (10) and that said central control unit (30) has a display and/or keyboard (33) connected to it.

8. An apparatus as defined in claim 1, in which apparatus the soft-tissue filter assembly (10) comprises a first body part (16) movable along horizontal linear guides (17a) in a horizontal plane transverse to the x-ray beam (XR) in conjunction with a second body part (18), said second body part (18) being supported from above at a lower end of a vertical section (12b) of a C-arm of a panoramic radiographic apparatus, characterized in that a wedge-shaped soft-tissue filter element (19) is operatively associated with an end of said first body part so as to make a tip edge (19a) of the filter element horizontally adjustable to the same plane (R) passing through the focus (F) of the x-ray source with which plane the light marker line (LL) projected from said light indicator unit (20) is coincident on the side of the face of patient (P).

9. An apparatus as defined in claim 1, characterized in that said apparatus comprises at least two superimposed soft-tissue filter elements ($19_1$–$19_N$) (N elements), each arranged to be movable by an individual drive motor ($15_1$–$15_N$), and that, correspondingly, the light indicator unit (20) is adapted to house at least two superimposed light marker line units (N units), each connected to control the drive motor ($15_1$–$15_N$) of its own soft-tissue filter element ($19_1$–$19_N$) in a manner permitting the implementation of varied staircase or other stepped profiles of soft-tissue faltering different from a straight line.

10. An apparatus as defined in claim 1, characterized in that said apparatus comprises at least two soft-tissue filter assemblies (10, OB) acting successively, each filter assembly being controllable in response to an individual light indicator unit (20) so as to implement soft-tissue filter profiles adjustable in the horizontal direction without the need for changing the filter element (19).

* * * * *